United States Patent
Hashimoto et al.

(10) Patent No.: US 8,743,031 B2
(45) Date of Patent: Jun. 3, 2014

(54) DIBENZOTHIOPHENE COMPOUND AND ORGANIC LIGHT-EMITTING ELEMENT BASED ON THE SAME

(75) Inventors: Masashi Hashimoto, Tokyo (JP); Jun Kamatani, Tokyo (JP); Kenichi Ikari, Kawasaki (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 308 days.

(21) Appl. No.: 13/232,287

(22) Filed: Sep. 14, 2011

(65) Prior Publication Data
US 2012/0075171 A1 Mar. 29, 2012

(30) Foreign Application Priority Data
Sep. 29, 2010 (JP) .................. 2010-219481

(51) Int. Cl.
| | |
|---|---|
| G09G 3/32 | (2006.01) |
| H01L 27/32 | (2006.01) |
| H01L 51/54 | (2006.01) |
| C07D 333/76 | (2006.01) |
| C07D 409/14 | (2006.01) |

(52) U.S. Cl.
USPC ................. 345/80; 549/43; 548/440; 257/40; 257/E51.024; 257/E27.119

(58) Field of Classification Search
USPC ................. 345/80; 549/43; 548/440; 257/40, 257/E51.024, E27.119
See application file for complete search history.

(56) References Cited

FOREIGN PATENT DOCUMENTS

| | | |
|---|---|---|
| JP | 2009-267257 A | 11/2009 |
| WO | 2006-137210 A1 | 12/2006 |
| WO | 2009-021126 A2 | 2/2009 |
| WO | 2009-085344 A2 | 7/2009 |

*Primary Examiner* — Kristin Vajda
(74) *Attorney, Agent, or Firm* — Canon U.S.A., Inc., IP Division

(57) ABSTRACT

An aspect of the present invention provides the dibenzothiophene compound expressed by General Formula 1 in Claim 1. In General Formula 1, $R_1$ is either a hydrogen atom or an unsubstituted phenyl group, and $Ar_1$ is any of phenanthrenyl, fluorenyl, triphenylenyl, naphthyl, chrysenyl, and pyrenyl groups. The options for the $Ar_1$ substituents, namely the phenanthrenyl, fluorenyl, triphenylenyl, naphthyl, chrysenyl, and pyrenyl groups, may contain at least one of an alkyl group having one to four carbon atoms and an aryl group as a substituent.

12 Claims, 1 Drawing Sheet

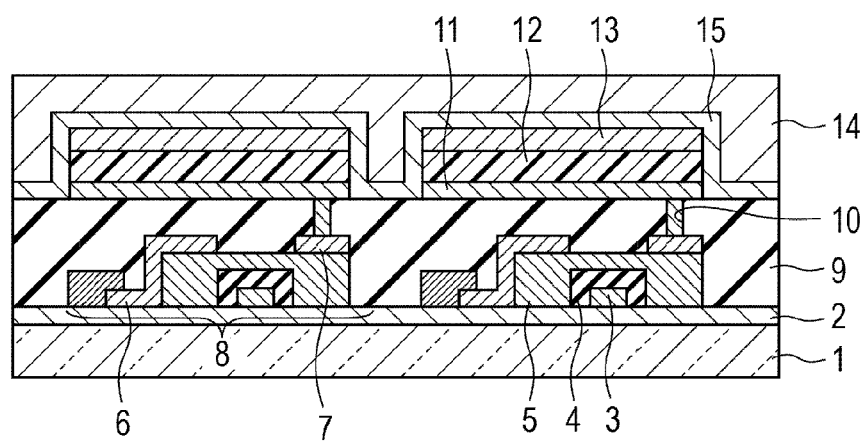

DIBENZOTHIOPHENE COMPOUND AND ORGANIC LIGHT-EMITTING ELEMENT BASED ON THE SAME

BACKGROUND OF THE INVENTION

1. Field of the Invention

The present invention relates to a dibenzothiophene compound and an organic light-emitting element based on this compound.

2. Description of the Related Art

Organic light-emitting elements have a cathode, an anode, and an organic compound layer located between these two electrodes. The electrodes individually inject holes and electrons into the organic compound layer, which in turn serves as a light-emitting layer where the holes and the electrons are coupled again and form excitons. These excitons then return to their ground state, and light is emitted thereby. There have been great advances in the organic light-emitting element technology in recent years, and now we can fabricate light-emitting devices with a light weight, a low profile, quick responses, various emission wavelengths, and a low driving-voltage requirement.

Organic phosphorescence-emitting elements are another type of organic light-emitting elements, which have a phosphorescence-emitting material in their light-emitting layer, and triplet excitons formed in this material release light.

International Publication Nos. WO 2009-085344, WO 2009-021126, WO 2006-137210, and Japanese Patent Laid-Open No. 2009-267257 (no foreign equivalents available) describe organic light-emitting elements with the following compounds as the host material.

Chemical Formula 1

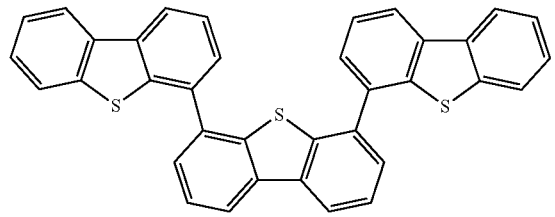

SS-1

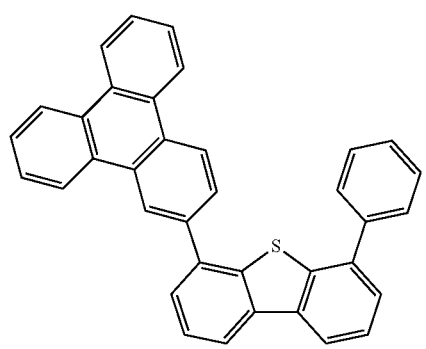

SS-2

Chemical Formula 2

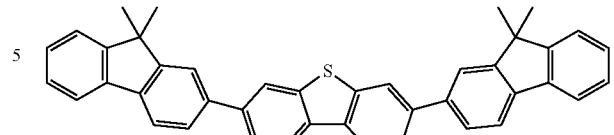

SS-3

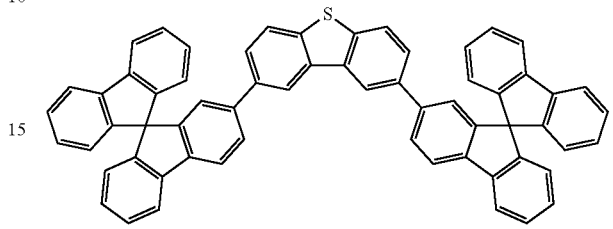

SS-4

Chemical Formula 3

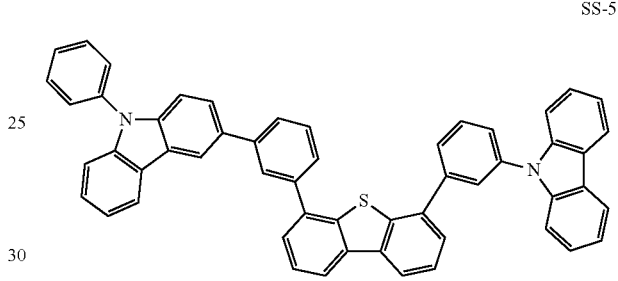

SS-5

International Publication No. WO 2009-085344 discloses a compound composed of dibenzothiophene and heterocycles introduced at the C4 and C5 positions (Compound SS-1). International Publication No. WO 2009-021126 discloses a compound composed of dibenzothiophene and different aryl substituents at the C4 and C5 positions (SS-2). International Publication No. WO 2006-137210 discloses two compounds composed of dibenzothiophene and a single kind of fused polycycle with the polycycles introduced at the C2 and C7 positions in one and at the C3 and C6 positions in the other (SS-3 and SS-4). And, Japanese Patent Laid-Open No. 2009-267257 discloses a compound having heterocycles with nitrogen-carbon bonds (SS-5).

Unfortunately, however, organic light-emitting elements based on these compounds have only a short operation life.

SUMMARY OF THE INVENTION

Aspects of the present invention provide a highly stable dibenzothiophene compound as well as an organic light-emitting element based on this compound and offering a high light-emission efficiency and a long operation life.

More specifically, aspects of the present invention provide a dibenzothiophene compound represented by General Formula 1 below.

Chemical Formula 4

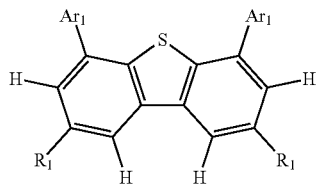

In General Formula 1, $R_1$ is either a hydrogen atom or an unsubstituted phenyl group, and $Ar_1$ is any of phenanthrenyl, fluorenyl, triphenylenyl, naphthyl, chrysenyl, and pyrenyl groups.

The options for the $Ar_1$ substituents, namely the phenanthrenyl, fluorenyl, triphenylenyl, naphthyl, chrysenyl, and pyrenyl groups, may comprise at least one of an alkyl group having one to four carbon atoms and an aryl group as a substituent.

Aspects of the present invention provide a highly stable dibenzothiophene compound as well as an organic light-emitting element based on this compound and offering a high light-emitting efficiency and a long operation life.

Further features of the present invention will become apparent from the following description of exemplary embodiments with reference to the attached drawing.

BRIEF DESCRIPTION OF THE DRAWINGS

The FIGURE is a schematic cross-sectional view of organic light-emitting elements and switching elements connected to them.

DESCRIPTION OF THE EMBODIMENTS

An embodiment of the present invention is a dibenzothiophene compound represented by General Formula 1 below.

Chemical Formula 5

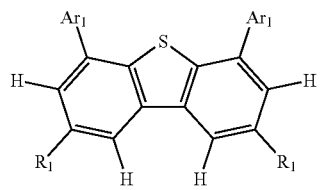

In General Formula 1, $R_1$ represents either a hydrogen atom or an unsubstituted phenyl group, and $Ar_1$ represents any of phenanthrenyl, fluorenyl, triphenylenyl, naphthyl, chrysenyl, and pyrenyl groups.

The options for the $Ar_1$ substituents, namely the phenanthrenyl, fluorenyl, triphenylenyl, naphthyl, chrysenyl, and pyrenyl groups, may comprise at least one of an alkyl group having one to four carbon atoms and an aryl group as a substituent.

Each $Ar_1$ substituent in General Formula 1 is a bulky polycyclic aromatic hydrocarbon, for example, a fused polycycle with three or more rings. Examples of fused polycycles having three or more rings include fluorenyl, phenanthrenyl, and triphenylenyl groups. These polycyclic aromatic hydrocarbons may contain an alkyl group having one to four carbon atoms or an aryl group as a substituent.

The two $Ar_1$ substituents in General Formula 1 are the same.

The $Ar_1$ groups in General Formula 1 may consist of a hydrocarbon with no heteroatoms. Heteroatoms have one or more lone pairs and thus often cause ionic impurities to contaminate the organic light-emitting element. Contamination with ionic impurities is considered to be a factor for degradation of organic light-emitting elements.

The substitution position numbers used hereinafter correspond to the position numbers defined in the structural formula below. This whole structure is referred to as the dibenzothiophene skeleton herein.

Chemical Formula 6

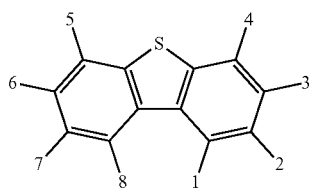

The dibenzothiophene compound according to this embodiment has polycyclic aromatic hydrocarbon groups at the substitution positions next to the sulfur atom, namely the C4 and C5 positions of dibenzothiophene. This is for the purpose of protecting the bonds between the sulfur atom of dibenzothiophene and the carbon atoms next to it.

In the first place, the region of bonding between the sulfur atom (S) in the dibenzothiophene skeleton and the carbon atoms on the benzene rings has the lowest bond energy in the skeleton. The bonds are thus the easiest to break in this molecule, and the broken bonds often trigger decomposition of the molecule. The dibenzothiophene derivative according to this embodiment has polycyclic aromatic hydrocarbon atoms at the C4 and C5 positions, so that the bonds between the sulfur atom (S) and the carbon atoms on the benzene rings can be protected from other molecules. The polycyclic aromatic hydrocarbon groups are bulky and thus can shelter the sulfur atom and the carbon atoms next to it through their effect of steric hindrance.

As a result, the bonds between the sulfur atom (S) and the carbon atoms on the benzene rings are kept from reacting with other molecules, and the compound is highly stable. The increased stability of the compound leads to a prolonged operation life of organic light-emitting elements based on the compound.

This is because this highly stable compound is unlikely to undergo alterations, a possible cause of a degraded operation of organic light-emitting elements.

The dibenzothiophene compound according to this embodiment has two pairs of active sites for electrophilic reactions, the C4 and C5 positions and the C2 and C7 positions. When the compound has substituents at the C2 and C7 positions besides the C4 and C5 positions, organic light-emitting elements based on the compound can have a further prolonged operation life; the C2 and C7 positions can be occupied by substituents, in particular, those with a low reactivity.

With substituents at the C2 and C7 positions in addition to the C4 and C5 positions, however, the compound has an increased molecular weight. An increased molecular weight may result in the compound being thermally decomposed during vacuum deposition, a process for fabrication of organic light-emitting elements. Therefore, the substituents at the C2 and C7 positions can be ones with a small molecular weight and a low reactivity, for example, phenyl groups. When organic light-emitting elements are fabricated by vacuum deposition, these substituents may be hydrogen atoms, the chemical species with the smallest molecular weight.

In the dibenzothiophene compound according to this embodiment, the substituents at the C4 and C5 positions are the same.

Having a single kind of substituent at symmetric substitution positions, the dibenzothiophene compound according to this embodiment has a higher degree of symmetry than compounds with different substituents introduced. The high degree of symmetry allows the molecular orbitals (the highest occupied molecular orbital, HOMO and the lowest unoccupied molecular orbital, LUMO) to exist throughout the molecule. As a result, the dibenzothiophene compound according to this embodiment, when serving as a charge carrier or in its excited state in an organic light-emitting element, can diffuse the structural change across its entirety, reducing local alterations in its structure. Reduced local structural changes lead to a slower material degradation in the organic light-emitting element, and the organic light-emitting element can have a prolonged operation life.

The dibenzothiophene skeleton of the dibenzothiophene compound according to this embodiment has a lowest triplet level (T1) of 420 nm; the compound has a high T1.

Intrinsically, in order for an organic compound to be used in an organic phosphorescence-emitting element, the compound should have a high T1.

This means that the dibenzothiophene compound according to this embodiment can be used in an organic phosphorescence-emitting element, in particular, as the host material of the light-emitting layer or an electron transport material.

Here, the host material is defined as the compound having the largest relative weight in the light-emitting layer. The light-emitting layer also contains a guest material and an assistant material. The guest material, which has a smaller relative weight than the host material, is the main contributor to light emission, whereas the assistant material, which also has a smaller relative weight than the host material, helps the guest material emit light.

The T1 of a compound varies with the substituents the compound has. Thus, the inventors have focused on the T1 energy of the polycyclic aromatic hydrocarbons that can take the $Ar_1$ positions in General Formula 1.

Table 1 lists some polycyclic aromatic hydrocarbons with their T1 energy levels (wavelength-equivalent). These polycyclic aromatic hydrocarbons, namely naphthalene, phenanthrene, fluorene, triphenylene, chrysene, and pyrene, have high levels of T1 energy and can be used in this embodiment. Using substituents with a low T1 energy level leads to a decreased overall T1 of the compound.

Furthermore, if one wants a phosphorescence-emitting material that generates blue to green light, the dibenzothiophene compound according to this embodiment can have phenanthrene, fluorene, or triphenylene as the polycyclic aromatic hydrocarbon at its $Ar_1$ positions. Here, the range blue to green corresponds to the range of emission wavelength from 440 nm to 530 nm, inclusive.

The compound according to this embodiment has a T1 energy level of its dibenzothiophene skeleton of 420 nm; the T1 energy level of this compound is higher than those of blue-phosphorescence-emitting materials. This means that using this compound in the light-emitting layer or neighbors of an organic light-emitting element that generates blue to green light leads to an improved light-emission efficiency of the organic light-emitting element.

Moreover, the compound according to this embodiment is a chemically stable material. When used as the host material, this highly durable compound gives the organic light-emitting element a prolonged operation life.

TABLE 1

| | Structural formula | Wavelength-equivalent T1 energy |
|---|---|---|
| Naphthalene | | 472 nm |
| Phenanthrene | | 459 nm |
| Fluorene | | 422 nm |
| Chrysene | | 500 nm |
| Pyrene | | 589 nm |
| Triphenylene | | 427 nm |

The dibenzothiophene compound according to this embodiment has two identical polycyclic aromatic hydrocarbons located symmetrically in its dibenzothiophene skeleton.

First, introducing two identical substituents at the C1 and C8 positions is impossible because of a large degree of steric repulsion.

With substituents at the C3 and C6 positions, however, the dibenzothiophene skeleton and the conjugated system combine, leading to a low level of T1 energy.

If one wants an organic light-emitting element that generates blue or green phosphorescence, those dibenzothiophene compounds that have substituents at the C3 and C6 positions cannot be used.

In the arrangement where substituents exist at the C2 and C7 substitution positions, there is no steric repulsion, and the conjugated system and the dibenzothiophene skeleton do not combine. Compared with dibenzothiophene compounds having substituents at the C4 and C5 positions, however, those having substituents at the C2 and C7 positions have a low level of T1 energy. Thus, the C4 and C5 substitution positions are used in this embodiment.

Consequently, the dibenzothiophene compound according to this embodiment can be used in organic light-emitting elements that generate blue or green phosphorescence.

The dibenzothiophene compound according to this embodiment can be used in any one or more of the following layers of an organic light-emitting element: the hole transport layer, the light-emitting layer, the hole-and-exciton-blocking layer, and the electron transport layer. An organic light-emitting element based on this dibenzothiophene compound is another embodiment of the present invention and will be described later.

Examples of the Dibenzothiophene Compound according to this Embodiment

The following provides several possible structural formulae of the dibenzothiophene compound according to this embodiment.

Chemical Formula 7

A-1
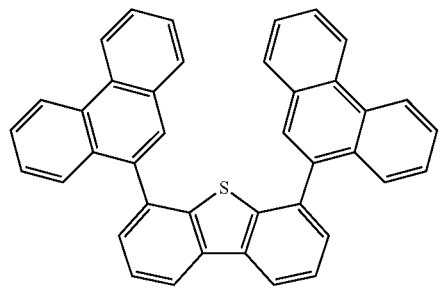

A-2
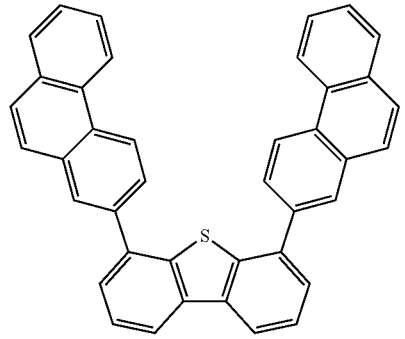

A-3
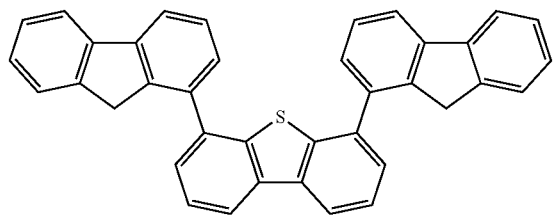

A-4
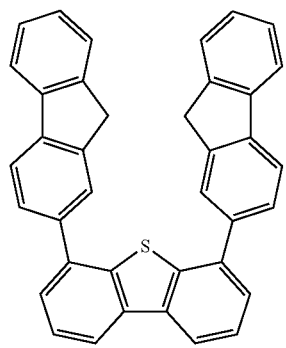

-continued

A-5
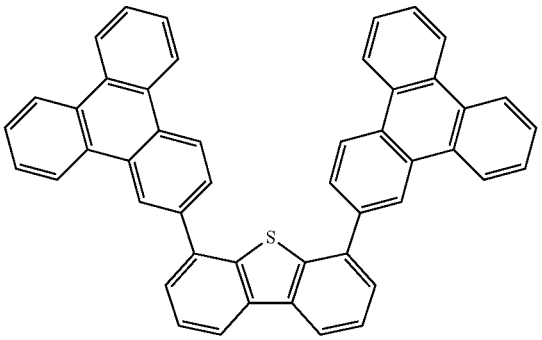

A-6
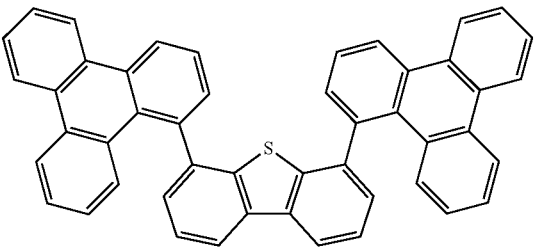

A-7
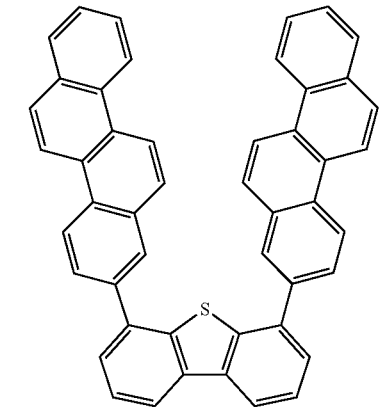

A-8
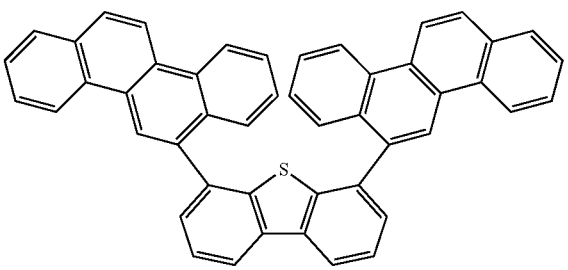

A-9
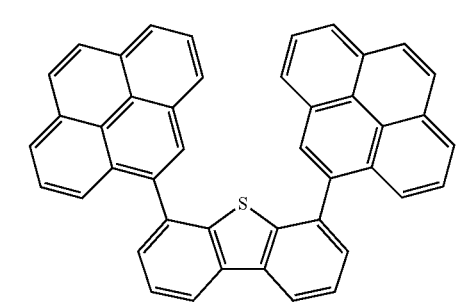

Chemical Formula 8
B-1 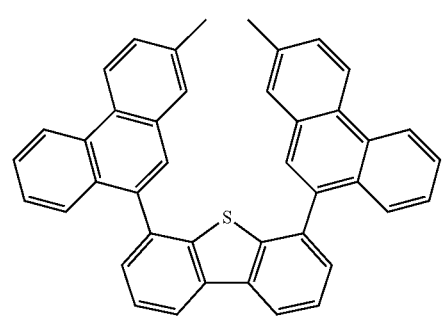
B-5 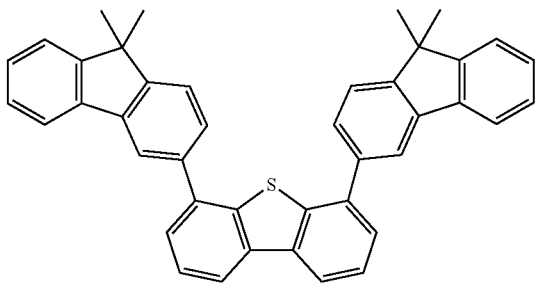
B-2 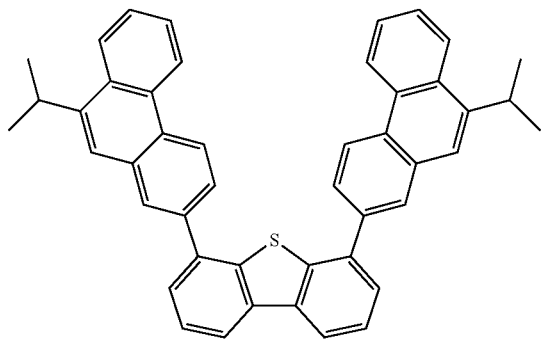
B-6 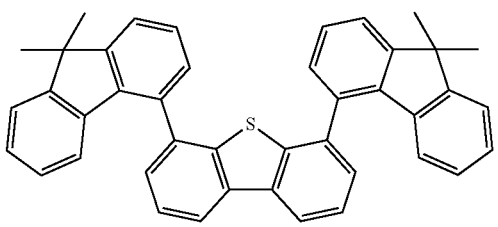
B-7 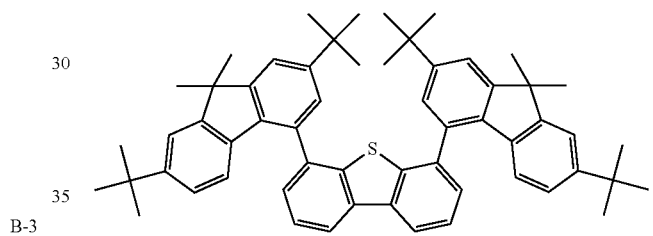
B-3 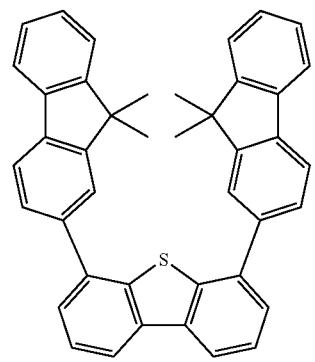
B-8 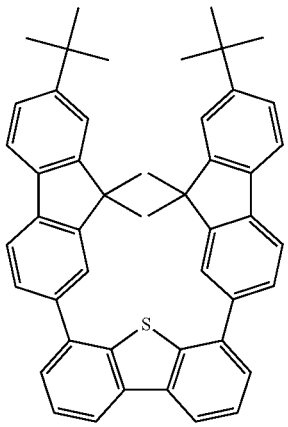
B-4 
B-9 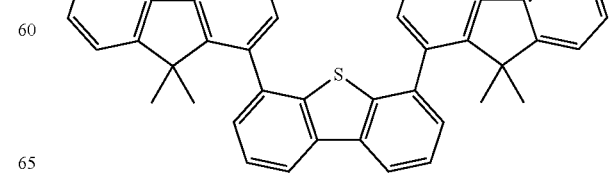

Chemical Formula 9
B-10
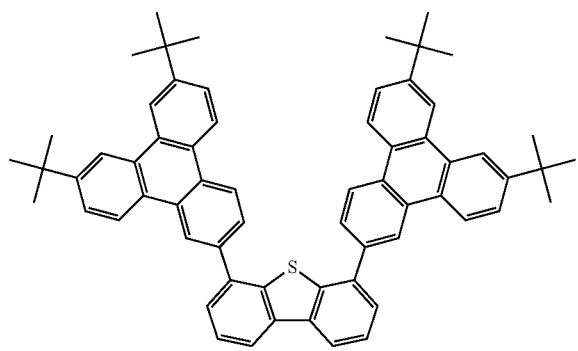
C-2
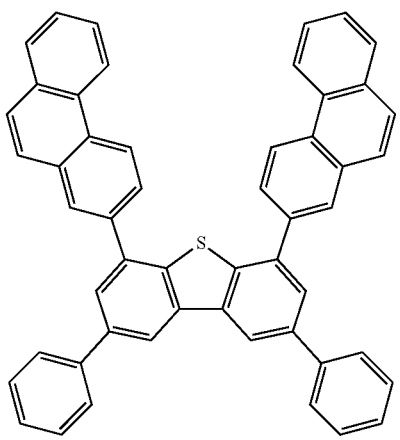
B-11
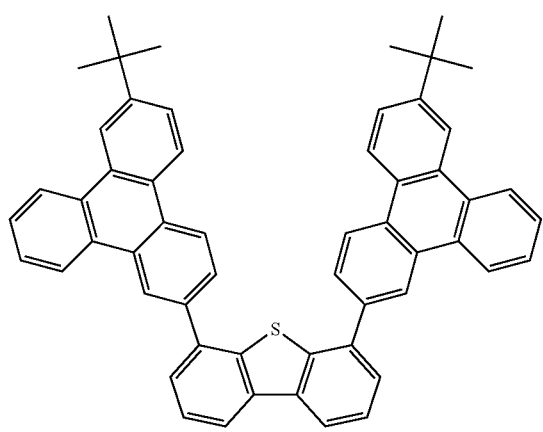
C-3
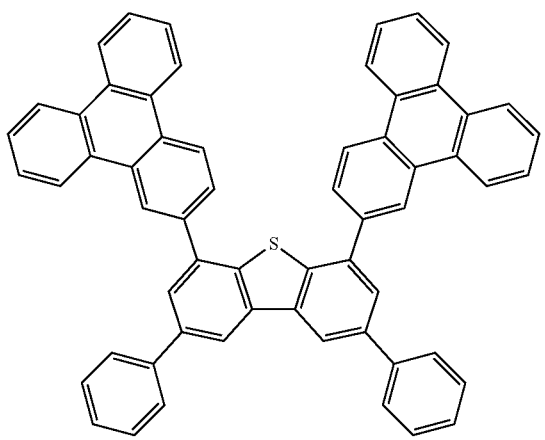
Chemical Formula 10
C-1
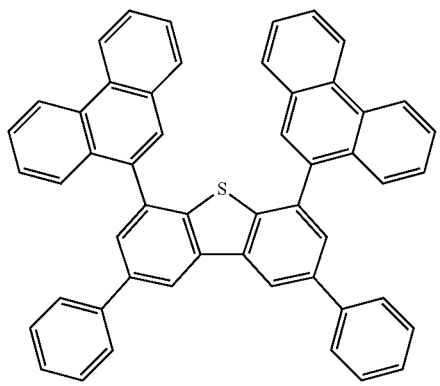
C-4
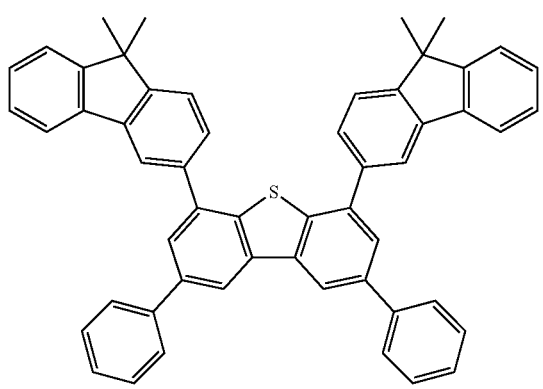

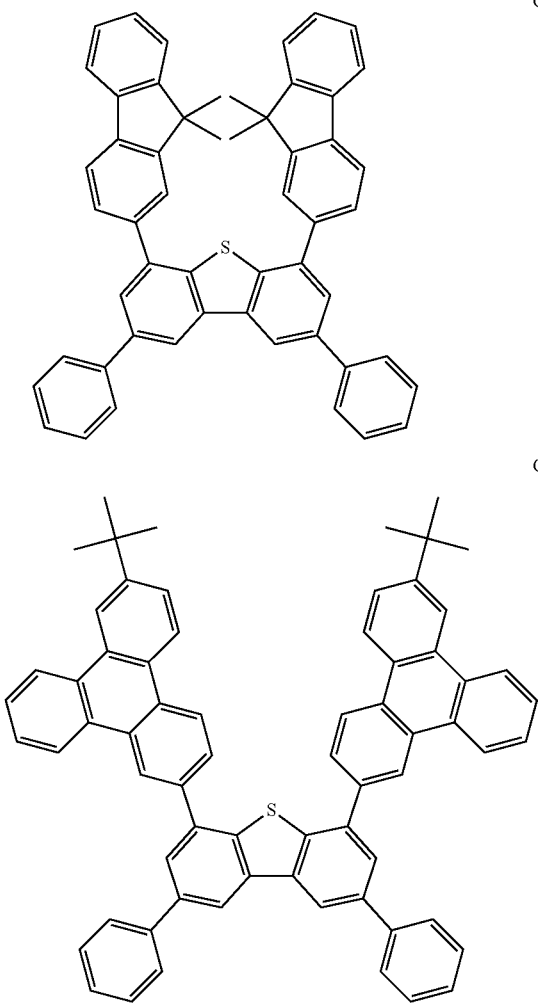
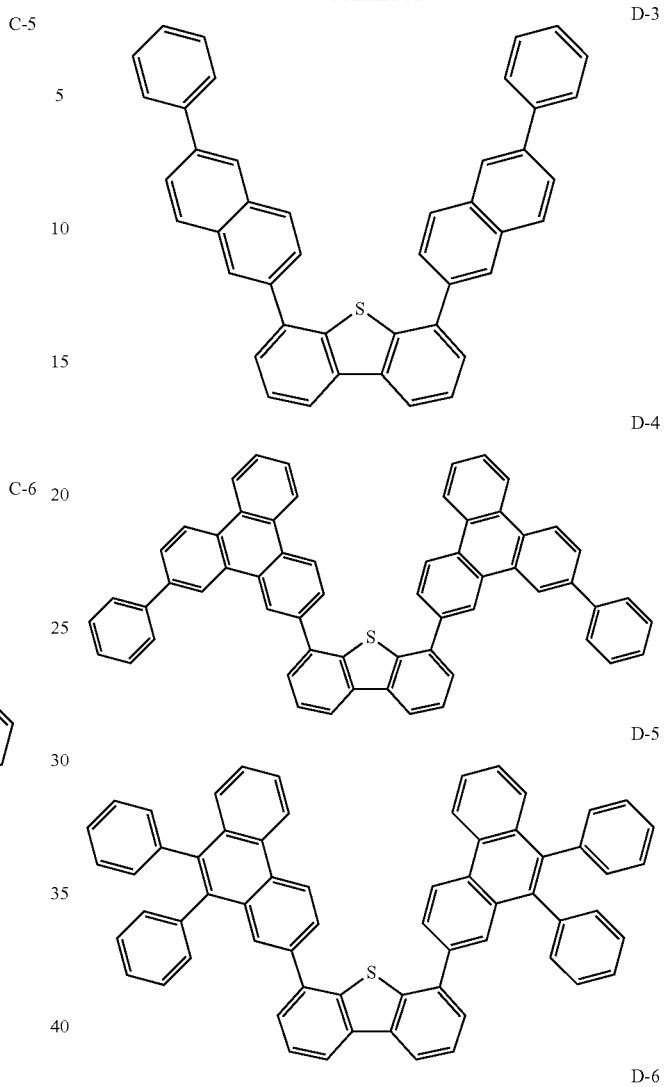
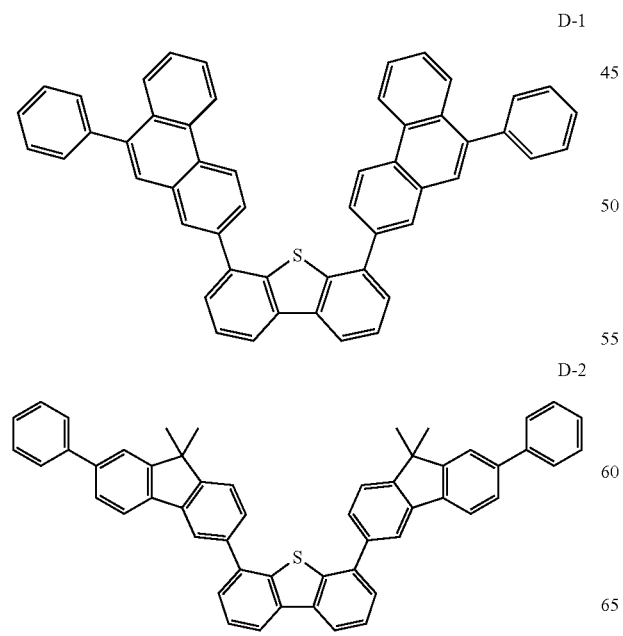
The compounds in Group A have unsubstituted polycyclic aromatic hydrocarbons at the $Ar_1$ positions specified in General Formula 1. These Group-A compounds have a high chemical stability and electron transport properties.
With any of these compounds or similar one as the electron transport material or the host or assistant material in the light-emitting layer, therefore, organic light-emitting elements can have a prolonged operation life.

The compounds in Group B have alkyl-substituted polycyclic aromatic hydrocarbons at the $Ar_1$ positions specified in General Formula 1. These Group-B compounds can form extremely stable film. With any of these compounds or similar one as the electron transport material or the host or assistant material in the light-emitting layer, therefore, organic light-emitting elements can have a prolonged operation life. The substituting hydrocarbons can be 9,9-dimethylfluorene. A small increase in molecular weight leads to greatly improved film formation properties.

The compounds in Group C are derivatives of some in Groups A and B and have phenyl groups at the C2 and C7 positions as additional substituents. In other words, these compounds have their active sites on the dibenzothiophene skeleton capped with the phenyl groups; these Group-C compounds are more chemically-stable than those in Groups A and B. With any of these compounds or similar one as the electron transport material or the host or assistant material in the light-emitting layer, therefore, organic light-emitting elements can have a prolonged operation life.

The compounds in Group D have aromatic-hydrocarbon-added polycyclic aromatic hydrocarbons at the $Ar_1$ positions specified in General Formula 1. These Group-D compounds can form stable film. With any of these compounds or similar one as the electron transport material or the host or assistant material in the light-emitting layer, therefore, organic light-emitting elements can have a prolonged operation life.

Table 2 summarizes the expected characteristics of these groups of exemplary compounds in comparison with those of Group A. Evaluations are expressed by symbols ⊙, ○, and Δ, with the compounds in Group A as the reference standard.

The symbols ⊙, ○, and Δ mean that the compounds in that group are superior, equal, and somewhat inferior to those in Group A in that category.

TABLE 2

| Compound group | Stability | Film formation | Ease of sublimation |
| --- | --- | --- | --- |
| Group A | ○ | ○ | ○ |
| Group B | ○ | ⊙ | ⊙ |
| Group C | ⊙ | ○ | Δ |
| Group D | ○ | ⊙ | Δ |

The most important types of characteristics of materials for organic light-emitting elements are the stability, film formation properties, and ease of sublimation of the compounds contained. Considering these three types of characteristics together, the compounds in Group B are the best for use as materials for organic light-emitting elements.

Synthesis Methods of the Dibenzothiophene Compound According to this Embodiment

The following describes a method for synthesizing the dibenzothiophene compound according to this embodiment.

In a possible synthesis method, the dibenzothiophene compound according to this embodiment is synthesized as illustrated in Chemical Formula 12 below, or more specifically by a coupling reaction involving a Pd-based catalyst and one of the following combinations: halogenated (X) dibenzothiophene and a boronic acid/boronate having the substituent ($Ar_1$); a halogenated (X) form of the substituent ($Ar_1$) and a boronic acid/boronate having dibenzothiophene. In this formula, $R_1$ is either a hydrogen atom or a phenyl group. Note that the dibenzothiophene compound according to this embodiment can also be synthesized in other ways. The following is an exemplary route of synthesis.

Exemplary Route of Synthesis

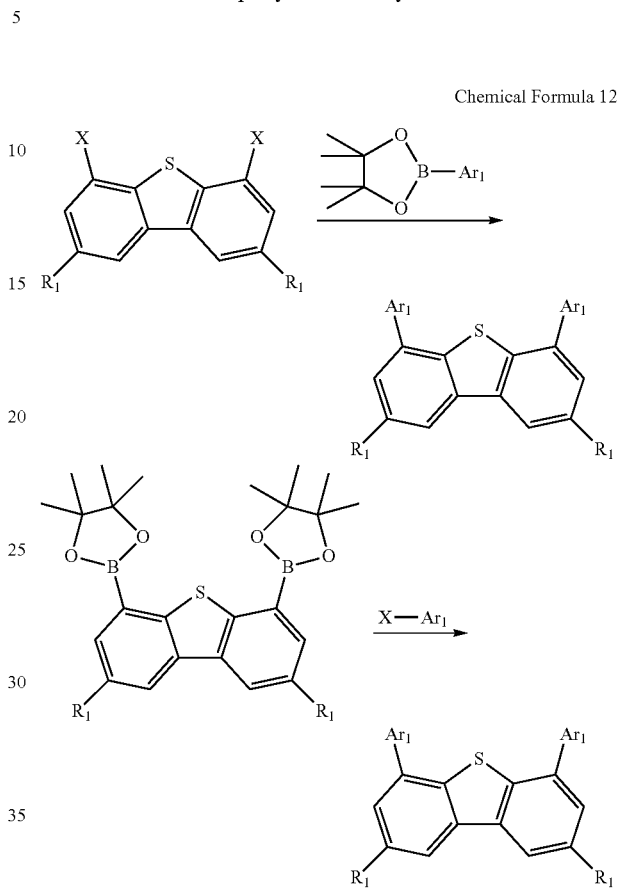

Chemical Formula 12

In this exemplary route of synthesis, $Ar_1$ is any of phenanthrenyl, fluorenyl, and triphenylenyl groups.

In addition, the dibenzothiophene compound according to this embodiment, if it is to be used in organic light-emitting elements, can be purified by sublimation. This is because purification by sublimation is a highly effective way of improving the purity of organic compounds. However, purification by sublimation requires a higher temperature as the molecular weight of the organic compound increases, and the higher the temperature is, the more likely thermal decomposition and other unwanted events are to occur. The molecular weight of organic compounds used in organic light-emitting elements may be equal to or smaller than 1000; such small organic compounds can be purified by sublimation with no excessive heating needed.

Organic Light-Emitting Element, another Embodiment of the Present Invention

The following describes another embodiment of the present invention, an organic light-emitting element.

The organic light-emitting element according to this embodiment has a cathode and an anode, a typical form of electrode pair, and an organic compound layer located between them. This organic compound layer contains the organic compound according to aspects of the present invention.

The organic light-emitting element according to this embodiment may have two or more organic compound layers. If two or more organic compound layers are used, hole injection, hole transport, light-emitting, hole-blocking, exciton-blocking, electron transport, electron injection, and other layers can also be used in combination.

The organic light-emitting element can contain the dibenzothiophene compound according to the previous embodiment in its organic compound layer or some or all of its organic compound layers regardless of layer constitution. For example, the organic light-emitting element can contain the dibenzothiophene compound as the host material in its light emitting layer.

When the dibenzothiophene compound according to the previous embodiment is used in a phosphorescence-emitting element as the electron transport material or the host or assistant material in the light-emitting layer, the phosphorescence-emitting material for use as the guest material is a metal complex based on iridium, platinum, rhenium, copper, europium, ruthenium, or any other similar metal. In particular, iridium complexes can generate intense phosphorescence. The light-emitting layer may contain two or more phosphorescence-emitting materials for assisted transmission of excitons and carriers.

In the organic light-emitting element according to this embodiment, the concentration of the guest material in the light-emitting layer is in the range of 0.01 wt % to 50 wt %, inclusive, and even in the range of 0.1 wt % to 20 wt %, inclusive, relative to the total weight of the constituent materials for the light-emitting layer. In one aspect, the concentration of the guest material is in the range of 0.1 wt % to 10 wt %, inclusive, so that concentration quenching can be curbed.

In the light-emitting layer, the guest material may be distributed uniformly in the whole layer, have some concentration gradient, or be limited to a particular region to leave some region free of it.

Specific examples of the metal complexes that can be used in the phosphorescence-emitting material in aspects of the present invention are, but not limited to, the following.

Chemical Formula 13

Ir-1

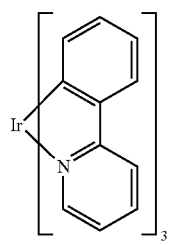

Ir-2

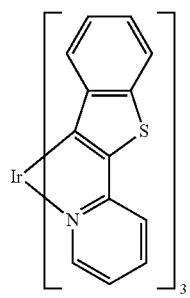

Ir-3

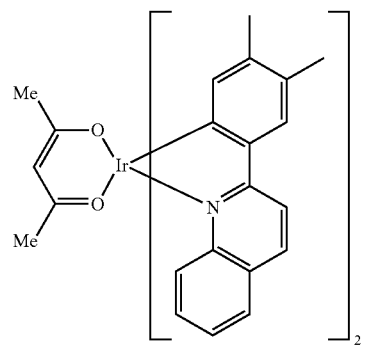

Ir-4

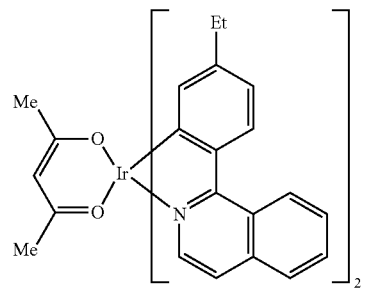

Ir-5

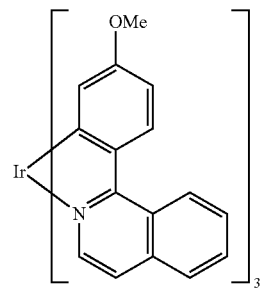

Ir-6

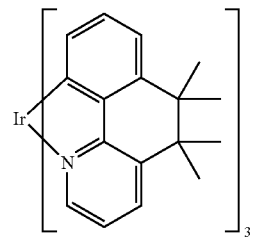

Ir-7

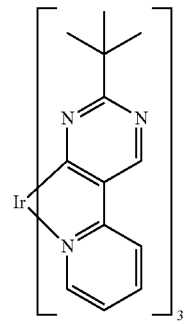

-continued
Ir-8
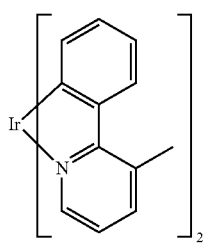
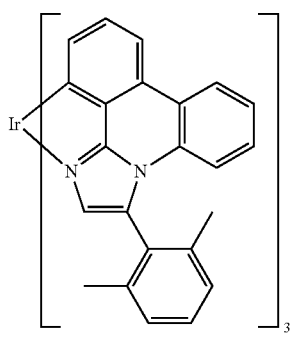
Ir-9
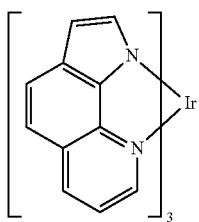
Ir-10
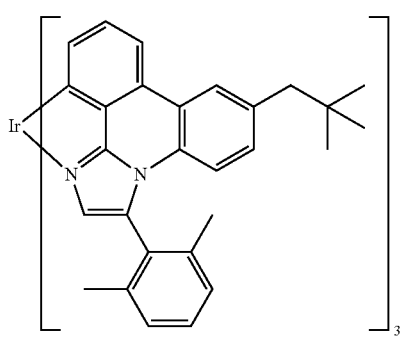
Ir-11
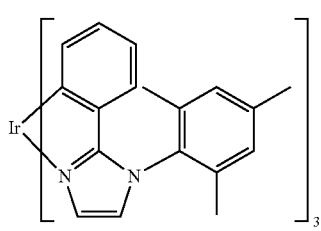
Ir-12
-continued
Chemical Formula 14
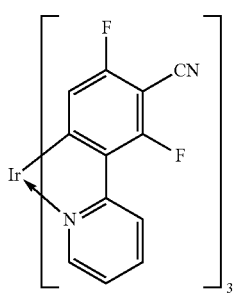
Ir-13
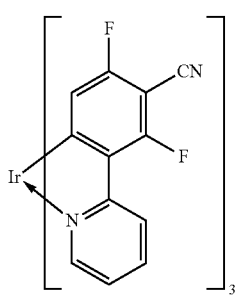
Ir-14
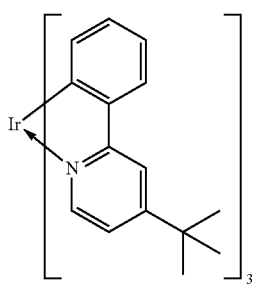
Ir-15
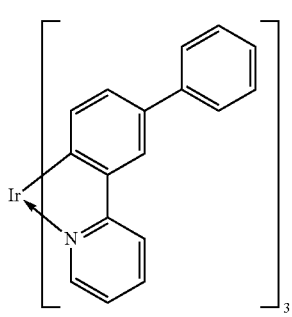
Ir-16
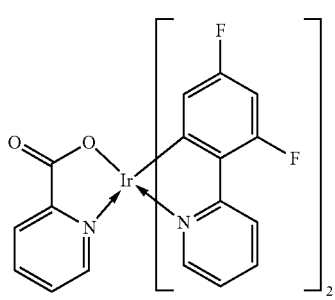
Ir-17

-continued
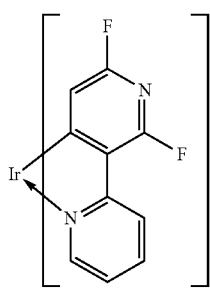
Ir-18
Chemical Formula 15
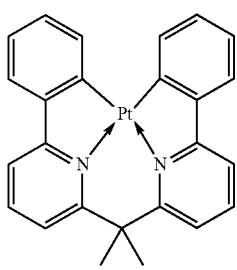
Pt-1
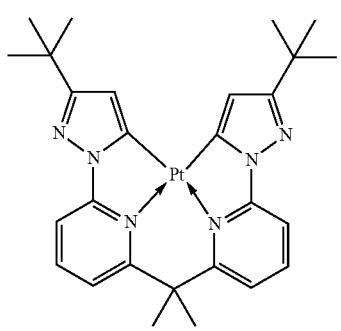
Pt-2
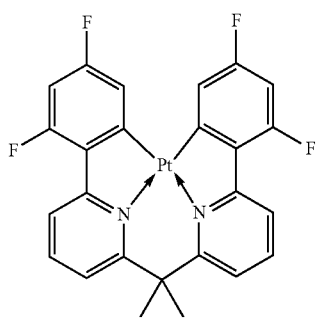
Pt-3
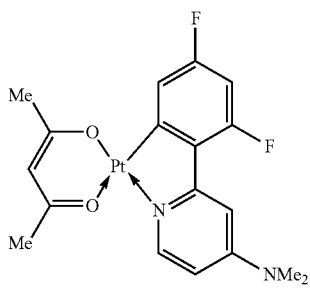
Pt-4
-continued
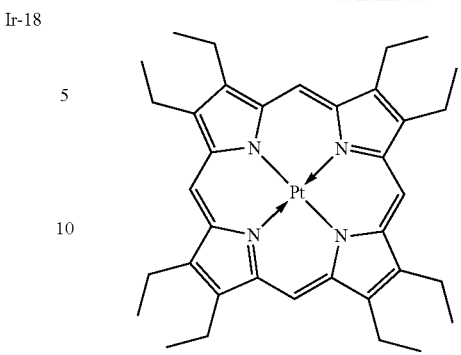
Pt-5
Chemical Formula 16
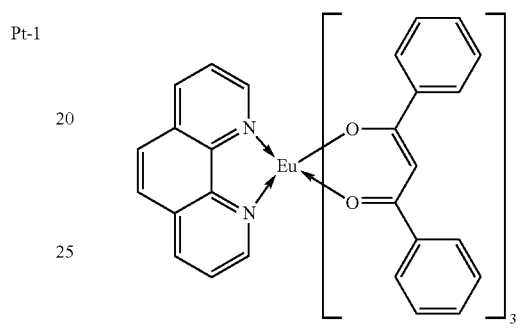
La-1
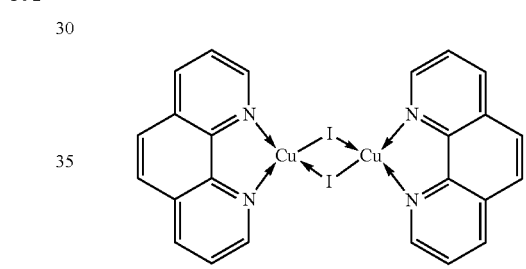
Cu-1
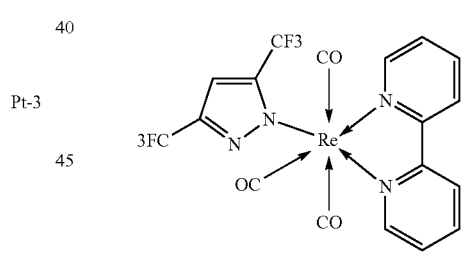
Re-1
Specific examples of the compounds that can be used in aspects of the present invention as the host material are, but not limited to, the following.
Chemical Formula 17
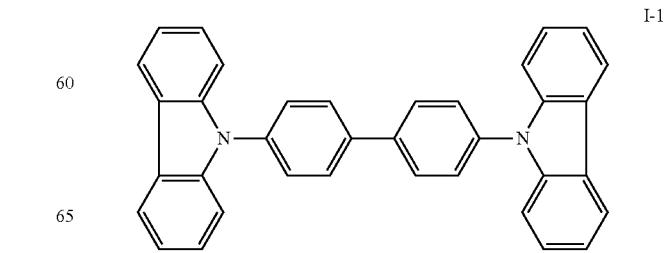
I-1

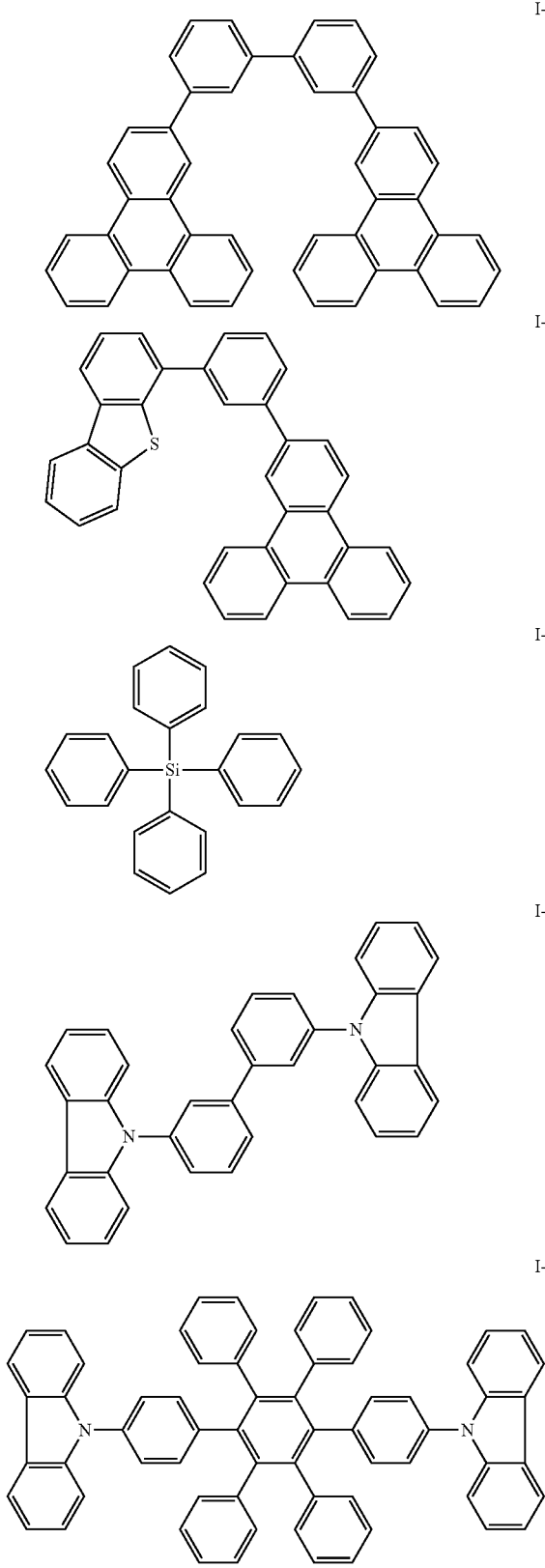

According to one aspect, any known low- and high-molecular-wright compounds may be used in addition to the compound according to aspects of the present invention. More specifically, compounds that can be used together with the compound according to aspects of the present invention include a hole injection/transport compound, a host-material compound, a light-emitting compound, an electron injection/transport compound, and so forth. The following provides some examples of these types of compounds.

The hole injection/transport compound can have a high degree of hole mobility so that holes can be easily injected from the cathode into it and that the injected holes can then be transported to the light-emitting layer. Examples of low- and high-molecular-weight compounds having hole injection/transport properties include triarylamine derivatives, phenylenediamine derivatives, stilbene derivatives, phthalocyanine derivatives, and porphyrin derivatives as well as poly (vinyl carbazole), polythiophene, and other conductive polymers.

The light-emitting compound is mainly responsible for the light-emitting function. Examples of this type of compound include, in addition to the above-mentioned phosphorescence-emitting compounds for use as the guest material and their derivatives, fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolate)aluminum, and organic beryllium complexes as well as poly(phenylene vinylene) derivatives, polyfluorene derivatives, polyphenylene derivatives, and other polymeric derivatives.

The electron injection/transport compound can be any compound into which electrons can be easily injected from the anode and from which the injected electrons can be transported to the light-emitting layer, and is chosen in consideration of factors such as the balance between its electron mobility and the hole injection/transport compound's hole mobility. Examples of compounds having electron injection/transport properties include oxadiazole derivatives, oxazole derivatives, pyrazine derivatives, triazole derivatives, triazine derivatives, quinoline derivatives, quinoxaline derivatives, phenanthroline derivatives, organic aluminum complexes, and so forth.

If possible, the material of the cathode is a compound with a high work function, for example, gold, platinum, silver, copper, nickel, palladium, cobalt, selenium, vanadium, tungsten, or any other similar pure metal, an alloy of two or more of these metals, or a metal oxide such as tin oxide, zinc oxide, indium oxide, indium tin oxide (ITO), or indium zinc oxide. Conductive polymers such as polyaniline, polypyrrole, and polythiophene can also be used. These electrode materials may be used alone or in combination of two or more kinds. Furthermore, the cathode may be a monolayer one or a multilayer one having two or more layers.

On the other hand, the material of the anode is a compound with a low work function, if possible. Examples include lithium and other alkali metals, calcium and other alkaline-earth metals, aluminum, titanium, manganese, silver, lead, chromium, and other similar pure metals, and so forth. Alloys of two or more of these pure metals can also be used. Moreover, ITO and other metal oxides can be used. These electrode materials can be used alone or in combination of two or more kinds. Furthermore, the anode may be a monolayer one or a multilayer one having two or more layers.

In the organic light-emitting element according to this embodiment, the layer(s) containing the organic compound according to the previous embodiment and, if any, the layer(s) based on any other organic compounds are usually formed as thin films by vacuum deposition, ionized-vapour deposition, sputtering, or plasma deposition, or by dissolving the constituting materials in an appropriate solvent and then applying the solution by any known technique (e.g., spin coating, dipping, casting, the LB method, or inkjet printing). When formed by vacuum deposition, coating with solution, or the like, the layer(s) is unlikely to undergo crystallization and other unwanted events and thus is remarkably resistant to degradation over time. Coating, furthermore, allows the constituting materials to be combined with an appropriate binder resin in the solution for film formation.

The binder resins that can be used here include, but not limited to, poly(vinyl carbazole) resin, polycarbonate resin, polyester resin, ABS resin, acrylic resin, polyimide resin, phenol resin, epoxy resin, silicone, urea resin, and so forth. These binder resins may be used alone as a homopolymer or a copolymer or in combination as a mixture of two or more kinds. Optionally, additives such as known plasticizers, antioxidants, and ultraviolet absorbers may also be added.

Applications of the Organic Light-Emitting Element

The organic light-emitting element according to aspects of the present invention can be used in display apparatuses and illumination apparatuses as well as in light sources for electrophotographic image-forming apparatuses, backlights of liquid-crystal display apparatuses, and so forth.

In a display apparatus, several pieces of the light-emitting element according to this embodiment are located in the display unit. The display unit has several pixels, and each pixel has a piece of the organic light-emitting element according to this embodiment and a TFT element, a typical form of switching elements for regulating luminance. The cathode or anode of the organic light-emitting element is connected to the drain electrode or source electrode of the TFT element. This display apparatus can be used in a PC or the like as an image display unit.

The display apparatus may be an image input apparatus; it receives image signals from an area CCD, a linear CCD, a memory card, or the like through its input unit and then outputs the input image to its display unit. Furthermore, the display apparatus may have, when in an imaging apparatus or an inkjet printer, both image output and signal input functions, the former for visualizing externally input image signals as a display unit and the latter for accepting orders to process the image as an operation panel. The display apparatus can also be used as the display unit of a multifunctional printer.

The following describes a display apparatus equipped with the organic light-emitting element according to this embodiment with reference to the FIGURE.

The FIGURE is a schematic cross-sectional view of the display apparatus, showing some pieces of the organic light-emitting element according to this embodiment and TFT elements, a typical form of switching elements, connected to them. This drawing includes two pairs of organic light-emitting elements and TFT elements. The following details this structure.

This display apparatus has a substrate 1 made of glass or any other appropriate material, and a moisture-proof film 2 extending over it to protect the TFT elements or the organic compound layer. The numeral 3 represents a gate electrode 3 made of metal, 4 a gate-insulating film 4, and 5 a semiconductor layer.

Each TFT element 8 has the semiconductor layer 5, a drain electrode 6, and a source electrode 7. The TFT elements 8 are covered with an insulating film 9. Each source electrode 7 is connected to the cathode 11 of each organic light-emitting element via a contact hole 10. Other constitutions of display apparatuses are also possible as long as either the cathode or anode of each organic light-emitting element is connected to either the source electrode or drain electrode of each TFT element.

Although the organic compound layer 12 looks like a monolayer one in this drawing, it in fact has a multilayer structure. The anodes 13 are covered with a first protection layer 14 and a second protection layer 15 so that degradation of the organic light-emitting elements can be prevented.

In such a display apparatus, yet another embodiment according to aspects of the present invention, no particular limitation is imposed on the switching elements; a single-crystal silicon substrate, MIM elements, a-Si type elements, and other types of switching elements can be used.

EXAMPLES

Synthesis Method 1, Synthesis of Compound A-5

Chemical Formula 18

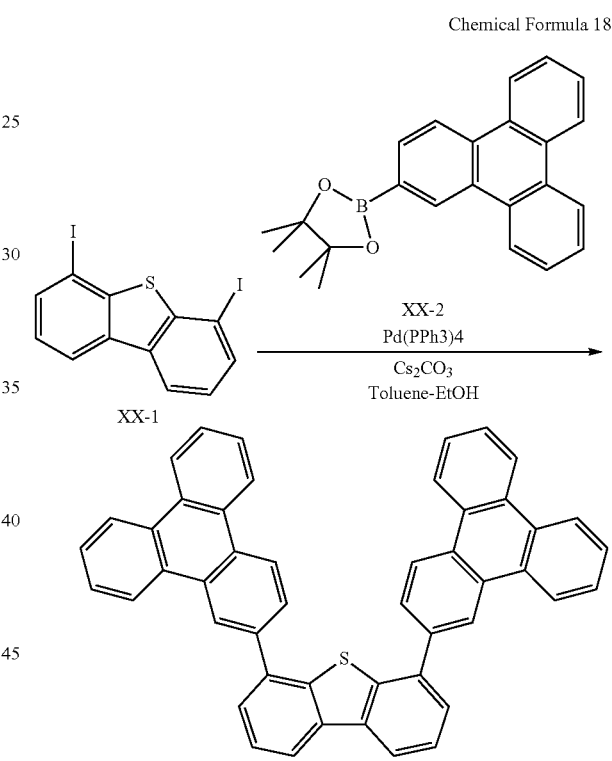

The reagents and solvents listed below were put into a 100-mL recovery flask:
XX-1: 500 mg (1.1 mmol);
XX-2: 1.0 g (2.9 mmol);
tetrakis(triphenyl phosphine)palladium (○): 133 mg (0.12 mmol);
toluene: 30 mL;
ethanol: 15 mL; and
30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The deposited crystals were collected by filtration and then washed in water, ethanol, and acetone to provide a crude product. This crude product was dissolved by heating in toluene, the obtained solution was filtered while still hot, and then the solute was recrystallized by adding toluene as the solvent to the solution. In this way, 642 mg of Compound A-5 was obtained (yield: 88%).

The identification of the obtained compound was confirmed by mass spectrometry.
MALDI-TOF-MS (matrix-assisted laser desorption/ionization–time-of-flight mass spectrometry)

Measured: m/z=636.21; calculated: $C_{28}H_{22}O$=636.19.

Then, the T1 energy of the obtained compound A-5 was determined in the following way.

The obtained compound A-5 was dissolved in toluene to provide a dilute solution, and then a phosphorescence spectrum was measured in an Ar atmosphere, at 77 K, and with an excitation wavelength of 350 nm. From the first emission peak wavelength of the obtained phosphorescence spectrum, the wavelength-equivalent T1 energy was determined to be 481 nm.

Synthesis Method 2, Synthesis of Compound B-4

Chemical Formula 19 was concentrated and then purified by separation in silica-gel column chromatography. A mixture of toluene and ethanol was added to the collected fraction of interest for the solute to be recrystallized. In this way, 642 mg of Compound B-4 was obtained (yield: 88%).

The identification of the obtained compound was confirmed by mass spectrometry.
MALDI-TOF-MS Measured: m/z=568.27; calculated: 568.22.

Then, the T1 energy of the obtained compound B-4 was determined in the same way as in Synthesis Method 1. The wavelength-equivalent value was 488 nm.

Synthesis Method 3, Synthesis of Compound C-2

Chemical Formula 20

The reagents and solvents listed below were put into a 100-mL recovery flask:
XX-1: 800 mg (1.8 mmol);
XX-3: 1.4 g (4.4 mmol);
tetrakis(triphenyl phosphine)palladium (○): 212 mg (0.18 mmol);
toluene: 30 mL;
ethanol: 15 mL; and
30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate The reagents and solvents listed below were put into a 200-mL recovery flask:
XX-4: 1.5 g (2.5 mmol);
XX-5: 1.9 g (6.1 mmol);
tetrakis(triphenyl phosphine)palladium (○): 295 mg (0.25 mmol);
toluene: 40 mL;
ethanol: 15 mL; and
30 wt % cesium carbonate aqueous solution: 15 mL.

The obtained reaction solution was heated and stirred under nitrogen to reflux for three hours. After the reaction was complete, water was added to the reaction solution, and the obtained mixture was stirred. The deposited crystals were collected by filtration and then washed in water and ethanol to provide a crude product. This crude product was dissolved by heating in toluene, the obtained solution was filtered while still hot, and then the solute was recrystallized by adding toluene as the solvent to the solution. In this way, 1.1 g of Compound C-2 was obtained (yield: 62%).

The identification of the obtained compound was confirmed by mass spectrometry.
MALDI-TOF-MS
Measured: m/z=688.30; calculated: 688.22.

Synthesis Method 4, Synthesis of Compound D-3

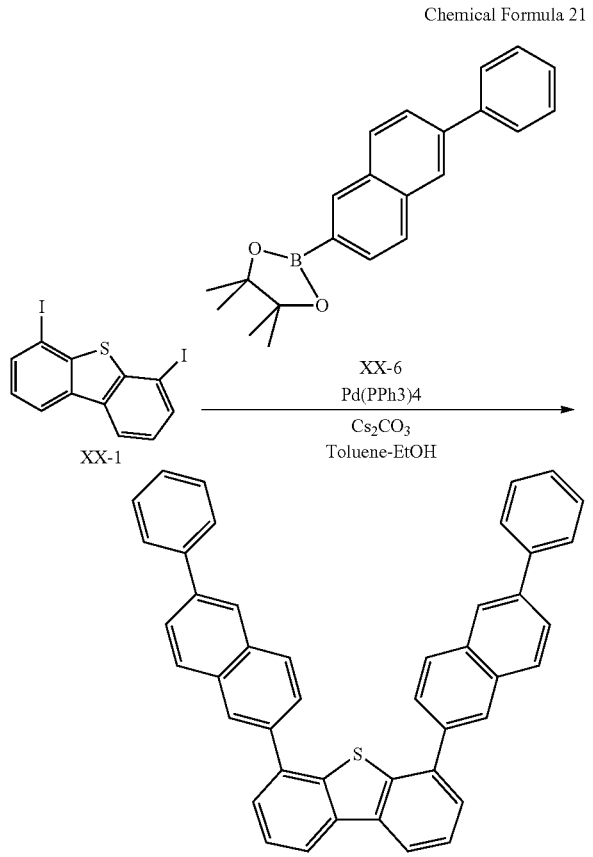

Chemical Formula 21

The reagents and solvents listed below were put into a 100-mL recovery flask:
XX-1: 650 mg (1.5 mmol);
XX-6: 1.1 g (3.6 mmol);
tetrakis(triphenyl phosphine)palladium (○): 172 mg (0.15 mmol);
toluene: 30 mL;
ethanol: 15 mL; and
30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The deposited crystals were collected by filtration and then washed in water and ethanol to provide a crude product. This crude product was dissolved by heating in toluene, the obtained solution was filtered while still hot, and then the solute was recrystallized by adding chlorobenzene as the solvent to the solution. In this way, 620 mg of Compound D-3 was obtained (yield: 70%).

The identification of the obtained compound was confirmed by mass spectrometry.

MALDI-TOF-MS
Measured: m/z=588.25; calculated: 588.19.

Synthesis Method 5, Synthesis of Compound C-3

Chemical Formula 22

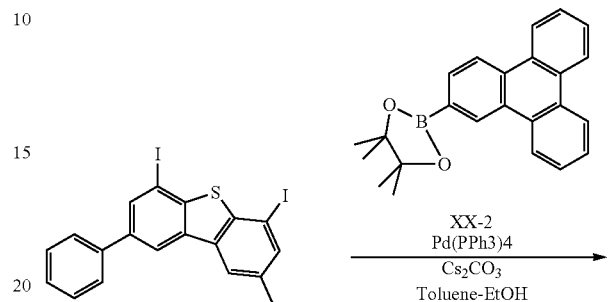

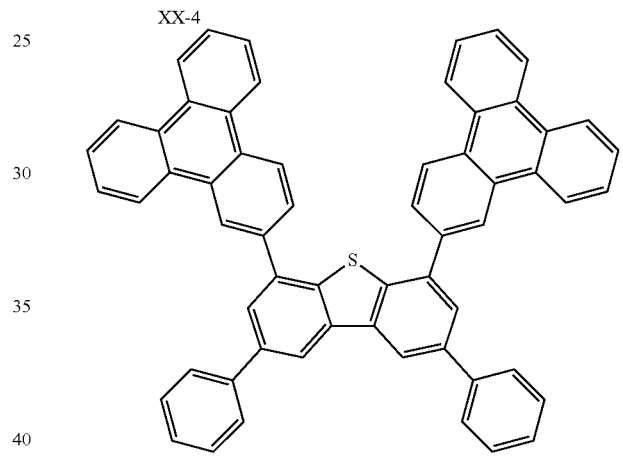

The reagents and solvents listed below were put into a 200-mL recovery flask:
XX-4: 2 g (3.4 mmol);
XX-2: 2.9 g (8.2 mmol);
tetrakis(triphenyl phosphine)palladium (○): 393 mg (0.34 mmol);
toluene: 50 mL;
ethanol: 25 mL; and
30 wt % cesium carbonate aqueous solution: 25 mL.

The obtained reaction solution was heated and stirred under nitrogen to reflux for three hours. After the reaction was complete, water was added to the reaction solution, and the obtained mixture was stirred. The deposited crystals were collected by filtration and then washed in water and ethanol to provide a crude product. This crude product was dissolved by heating in toluene, the obtained solution was filtered while still hot, and then the solute was recrystallized by adding toluene as the solvent to the solution. In this way, 1.1 g of Compound C-3 was obtained (yield: 62%).

The identification of the obtained compound was confirmed by mass spectrometry.
MALDI-TOF-MS
Measured: m/z=788.35; calculated: 788.25.

Synthesis Method 6, Synthesis of Compound A-2

Synthesis Method 7, Synthesis of Compound C-5

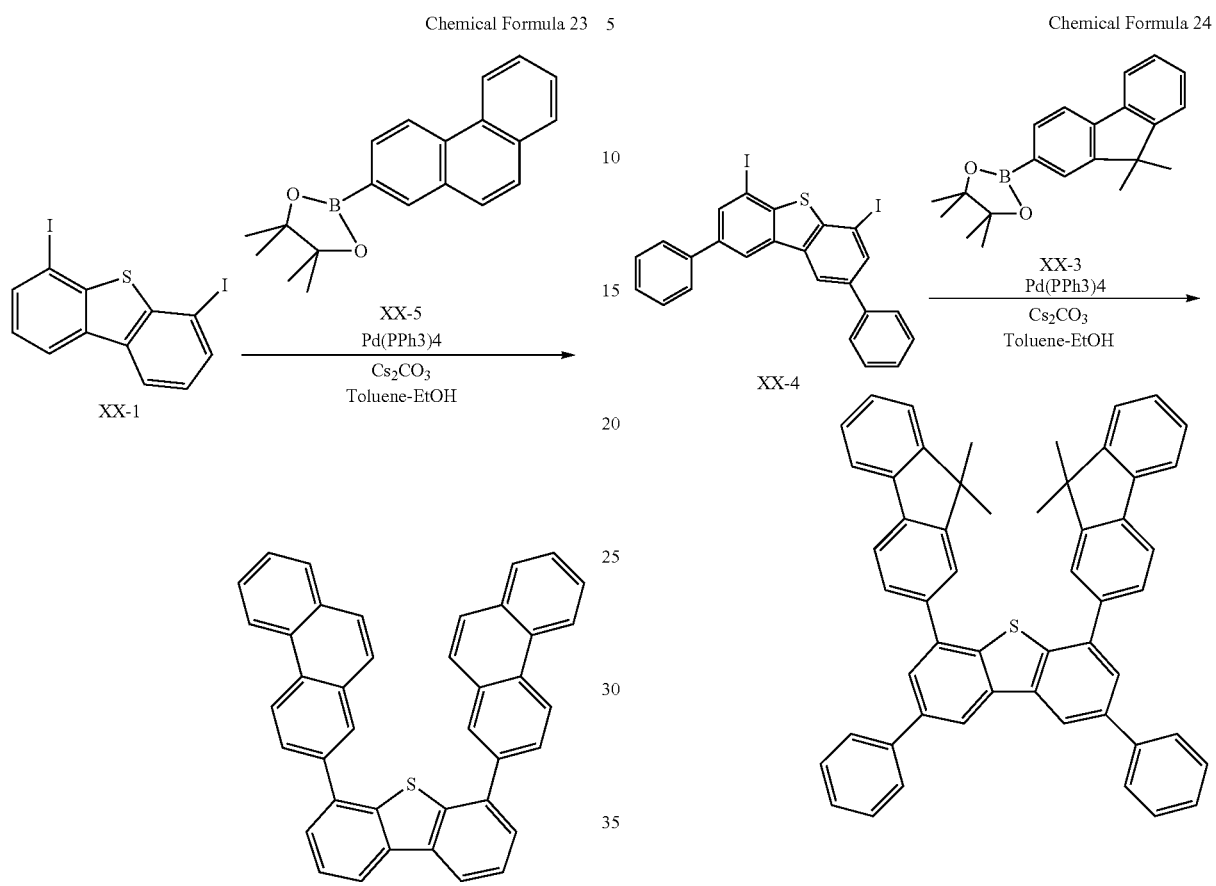

Chemical Formula 23

Chemical Formula 24

The reagents and solvents listed below were put into a 100-mL recovery flask:

XX-1: 1 g (2.3 mmol);
XX-5: 1.7 g (5.5 mmol);
tetrakis(triphenyl phosphine)palladium (○): 265 mg (0.23 mmol);
toluene: 30 mL;
ethanol: 15 mL; and
30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The deposited crystals were collected by filtration and then washed in water, ethanol, and acetone to provide a crude product. This crude product was dissolved by heating in toluene, the obtained solution was filtered while still hot, and then the solute was recrystallized by adding toluene as the solvent to the solution. In this way, 965 mg of Compound A-2 was obtained (yield: 78%).

The identification of the obtained compound was confirmed by mass spectrometry.
MALDI-TOF-MS The reagents and solvents listed below were put into a 100-mL recovery flask:

XX-4: 1 g (1.7 mmol);
XX-5: 1.3 g (4.1 mmol);
tetrakis(triphenyl phosphine)palladium (○): 196 mg (0.17 mmol);
toluene: 30 mL;
ethanol: 15 mL; and
30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate was concentrated and then purified by separation in silica-gel column chromatography. A mixture of toluene and ethanol was added to the collected fraction of interest for the solute to be recrystallized. In this way, 852 mg of Compound C-5 was obtained (yield: 70%).

The identification of the obtained compound was confirmed by mass spectrometry.
MALDI-TOF-MS Measured: m/z=720.40; calculated: 720.29.

Synthesis Method 8, Synthesis of Compound B-5

Synthesis Method 9, Synthesis of Compound A-1

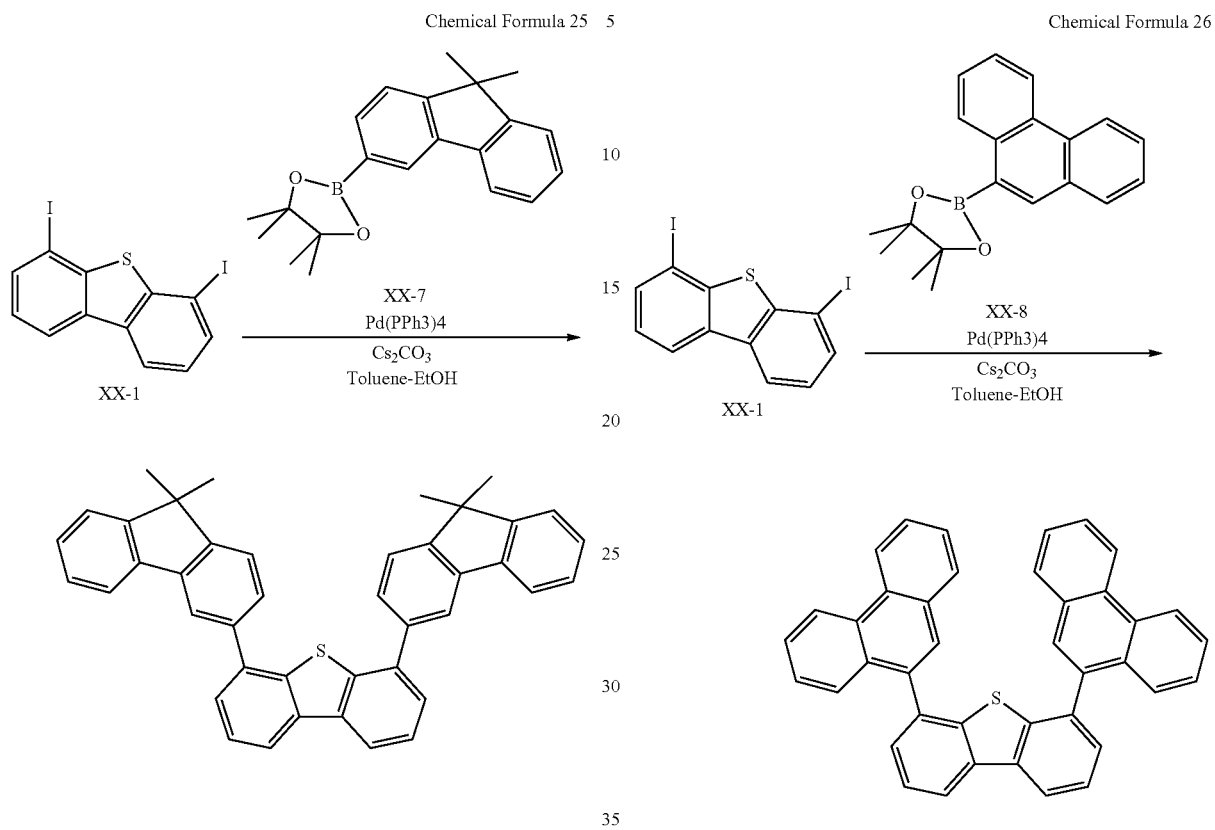

Chemical Formula 25

Chemical Formula 26

The reagents and solvents listed below were put into a 200-mL recovery flask:

XX-1: 1.2 g (2.8 mmol);

XX-7: 2.1 g (6.6 mmol);

tetrakis(triphenyl phosphine)palladium (○): 319 mg (0.27 mmol);

toluene: 50 mL;

ethanol: 20 mL; and 30 wt % sodium carbonate aqueous solution: 20 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate was concentrated and then purified by separation in silica-gel column chromatography. A mixture of toluene and ethanol was added to the collected fraction of interest for the solute to be recrystallized. In this way, 1.3 g of Compound B-5 was obtained (yield: 83%).

The identification of the obtained compound was confirmed by mass spectrometry.

MALDI-TOF-MS

Measured: m/z=560.50; calculated: 568.22.

The reagents and solvents listed below were put into a 100-mL recovery flask:

XX-1: 1.5 g (3.4 mmol);

XX-8: 2.5 g (8.3 mmol);

tetrakis(triphenyl phosphine)palladium (○): 398 mg (0.34 mmol);

toluene: 35 mL;

ethanol: 15 mL; and 30 wt % sodium carbonate aqueous solution: 15 mL.

The obtained reaction solution was heated and stirred under nitrogen to reflux for three hours. After the reaction was complete, water was added to the reaction solution, and the obtained mixture was stirred. The deposited crystals were collected by filtration and then washed in water, ethanol, and acetone to provide a crude product. This crude product was dissolved by heating in toluene, the obtained solution was filtered while still hot, and then the solute was recrystallized by adding toluene as the solvent to the solution. In this way, 1.1 g of Compound A-1 was obtained (yield: 59%).

The identification of the obtained compound was confirmed by mass spectrometry.

MALDI-TOF-MS

Measured: m/z=536.19; calculated: 536.16.

Synthesis Method 10, Synthesis of Compound B-7

Synthesis Method 11, Synthesis of Compound B-8

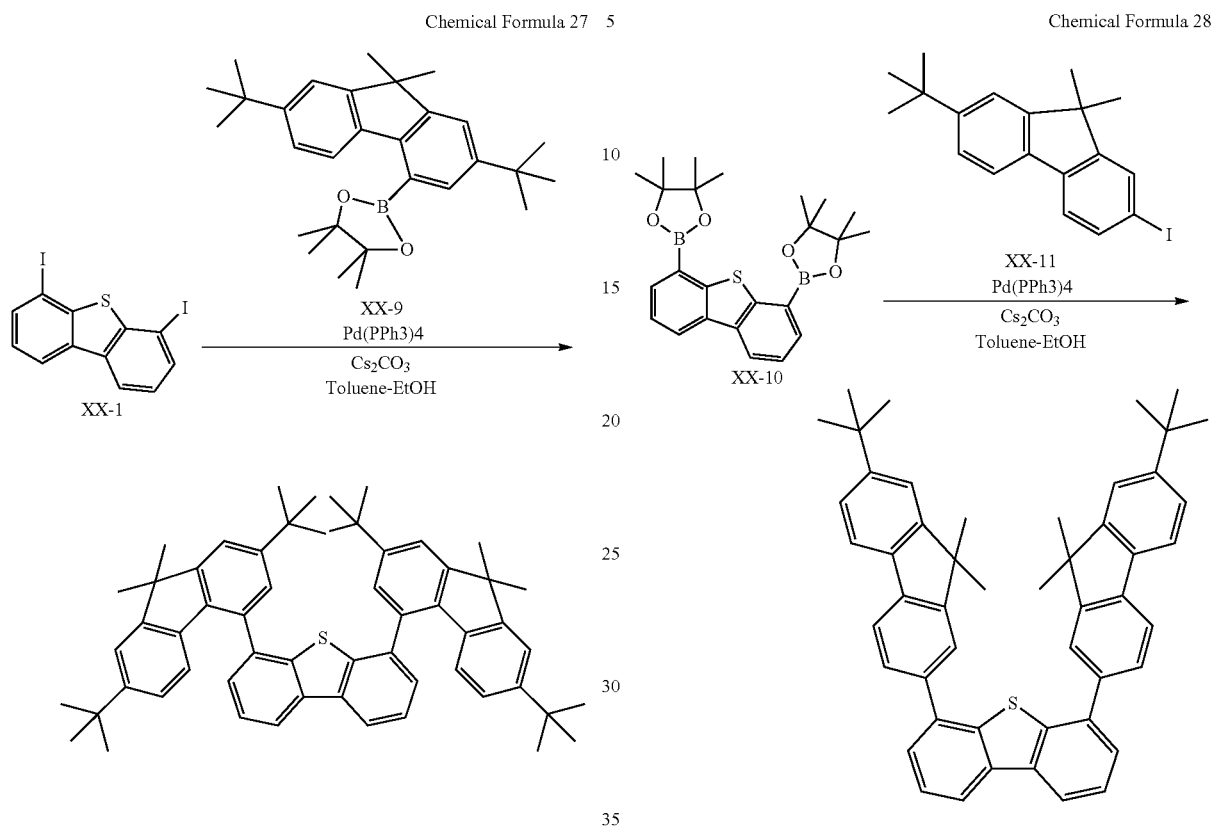

Chemical Formula 27

Chemical Formula 28

The reagents and solvents listed below were put into a 100-mL recovery flask:

XX-1: 1 g (2.3 mmol);

XX-9: 2.4 g (5.5 mmol);

tetrakis(triphenyl phosphine)palladium (○): 265 mg (0.23 mmol);

toluene: 30 mL;

ethanol: 15 mL; and 30 wt % cesium carbonate aqueous solution: 15 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate was concentrated and then purified by separation in silica-gel column chromatography. A mixture of toluene and ethanol was added to the collected fraction of interest for the solute to be recrystallized. In this way, 1.2 g of Compound B-7 was obtained (yield: 66%).

The identification of the obtained compound was confirmed by mass spectrometry.

MALDI-TOF-MS

Measured: m/z=792.60; calculated: 792.47.

The reagents and solvents listed below were put into a 100-mL recovery flask:

XX-10: 1 g (2.3 mmol);

XX-11: 2.1 g (5.5 mmol);

tetrakis(triphenyl phosphine)palladium (○): 265 mg (0.23 mmol);

toluene: 30 mL;

ethanol: 15 mL; and 30 wt % cesium carbonate aqueous solution: 15 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate was concentrated and then purified by separation in silica-gel column chromatography. A mixture of toluene and ethanol was added to the collected fraction of interest for the solute to be recrystallized. In this way, 1.3 g of Compound B-8 was obtained (yield: 83%).

The identification of the obtained compound was confirmed by mass spectrometry.

MALDI-TOF-MS

Measured: m/z=680.50; calculated: 680.35.

Synthesis Method 12, Synthesis of Compound A-9

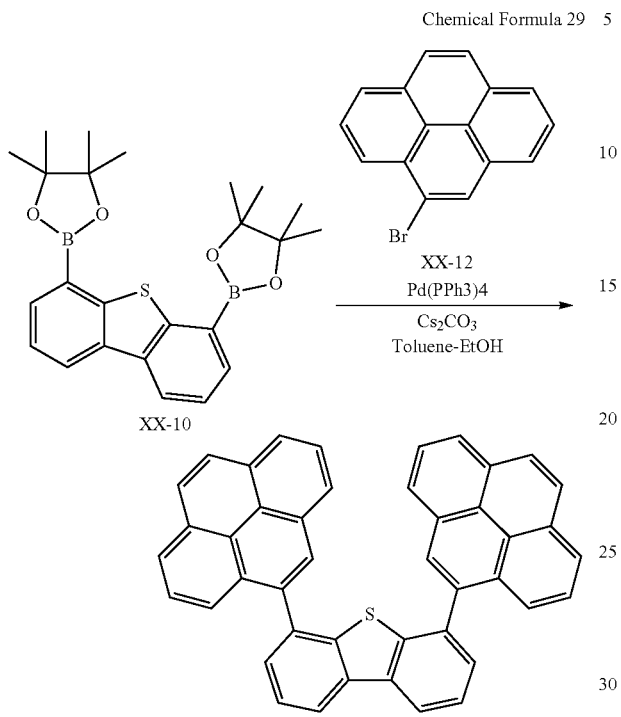

The reagents and solvents listed below were put into a 100-mL recovery flask:
XX-10: 1 g (2.3 mmol);
XX-12: 1 g (5.5 mmol);
tetrakis(triphenyl phosphine)palladium (○): 318 mg (0.28 mmol);
toluene: 30 mL;
ethanol: 15 mL; and
30 wt % cesium carbonate aqueous solution: 15 mL.

The obtained reaction solution was heated and stirred under nitrogen to reflux for three hours. After the reaction was complete, water was added to the reaction solution, and the obtained mixture was stirred. The solution was then allowed to cool to room temperature, extraction was performed with toluene, and the obtained organic layer was dried using magnesium sulfate. After the desiccant was filtered out, the filtrate was concentrated and then purified by separation in silica-gel column chromatography. A mixture of toluene and ethanol was added to the collected fraction of interest for the solute to be recrystallized. In this way, 468 mg of Compound A-9 was obtained (yield: 35%).

The identification of the obtained compound was confirmed by mass spectrometry.
MALDI-TOF-MS
Measured: m/z=584.49; calculated: 584.16.

Example 1

In each of the following examples, an organic light-emitting element was built on a substrate in the way described below. The light-emitting element had the following layers and electrodes formed in the following order: a cathode, a hole transport layer, a light-emitting layer, a hole-and-exciton-blocking layer, an electron transport layer, and an anode.

An ITO film, a cathode, was formed on a glass substrate by sputtering to a thickness of 120 nm to provide a transparent, conductive supporting substrate (the ITO substrate). On the ITO substrate, the following organic compound layers and electrode layers were sequentially formed by resistance-heating vacuum deposition in a vacuum chamber at $10^{-5}$ Pa, with the area of opposing electrodes set at 3 $mm^2$:

a hole transport layer (40 nm): HTL-1;
a light-emitting layer (30 nm): A-1 as the host material, and Ir-1 (10 wt %) as the guest material;
a hole-and-exciton-blocking layer (10 nm): omitted;
an electron transport layer (30 nm): ETL-1;
a first metal electrode layer (0.5 nm): LiF; and
a second metal electrode layer (100 nm): Al.

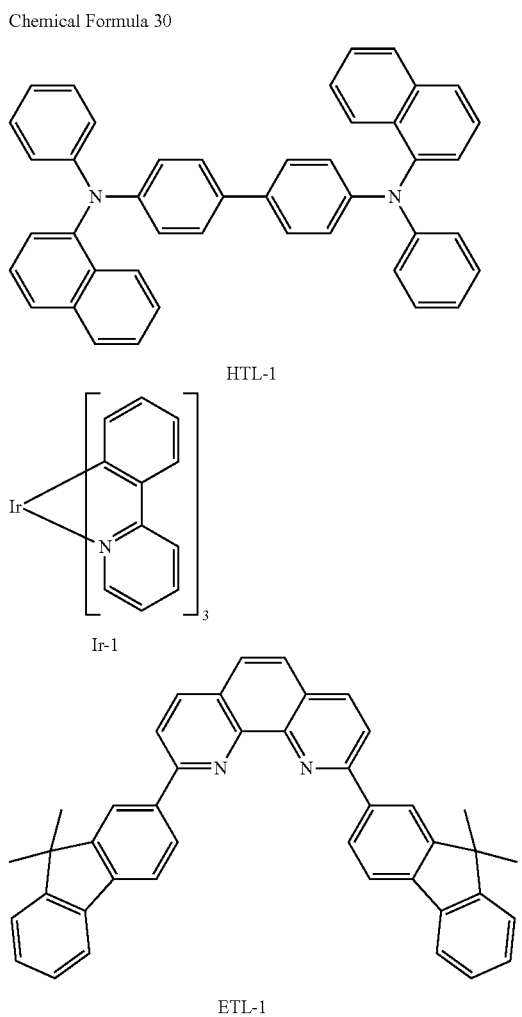

The obtained light-emitting element was covered with a glass plate and sealed with acrylic resin adhesive in dry air so as not to degrade on adsorption of moisture. In this way, an organic light-emitting element was completed.

The completed light-emitting element was subjected to a voltage of 4.7 V with the ITO electrode as the positive electrode and the Al electrode as the negative electrode. Green light was emitted with a light-emission efficiency of 51 cd/A and a luminance of 2500 cd/$m^2$. In this element, the CIE chromaticity coordinates were as follows: (x,y)=(0.30, 0.64).

Examples 2 to 15

Elements were fabricated in the same way as in Example 1 except that the host material and/or the guest material were/was changed and, in some examples, a hole-and-exciton-blocking layer was formed. The completed elements were tested in the same way as in Example 1. Results are summarized in Table 3.

TABLE 3

| | Host material | Guest material | Hole-and-exciton-blocking layer | Light-emission efficiency (cd/A) | Voltage (V) | Color of light |
|---|---|---|---|---|---|---|
| Example 2 | A-1 | Ir-16 | None | 40 | 6.0 | Green |
| Example 3 | A-2 | Ir-6 | None | 52 | 5.8 | Green |
| Example 4 | A-2 | Ir-1 | B-4 | 51 | 6.1 | Green |
| Example 5 | A-5 | Ir-1 | None | 56 | 5.5 | Green |
| Example 6 | A-9 | Pt-5 | None | 6 | 5.3 | Red |
| Example 7 | B-4 | Ir-15 | None | 50 | 4.9 | Green |
| Example 8 | B-5 | Ir-12 | None | 27 | 5.2 | Blue |
| Example 9 | B-5 | Ir-11 | B-5 | 11 | 5.5 | Blue |
| Example 10 | B-7 | Ir-7 | None | 8 | 6.5 | Blue |
| Example 11 | B-8 | Ir-1 | None | 55 | 5.3 | Green |
| Example 12 | C-2 | Ir-3 | None | 12 | 5.7 | Red |
| Example 13 | C-3 | Pt-1 | None | 45 | 5.0 | Green |
| Example 14 | C-5 | Ir-8 | None | 49 | 5.3 | Green |
| Example 15 | D-3 | Ir-4 | None | 11 | 5.2 | Red |

The results indicated that the dibenzothiophene compound according to aspects of the present invention, used in an organic phosphorescence-emitting element as an electron transport material or the material of the light-emitting layer, improved the light-emission efficiency. Examples 16 and 17, and Comparative Examples 1, 2, and 3

Elements were fabricated in the same way as in Example 1 except that the host material and the guest material were changed and that a hole-and-exciton-blocking layer was formed. The completed elements were tested for stability on the basis of their luminance half-life measured at a current of 40 mA/cm². Results are summarized in Table 4. The structures of the compounds used in the comparative examples were as follows.

Chemical Formula 31

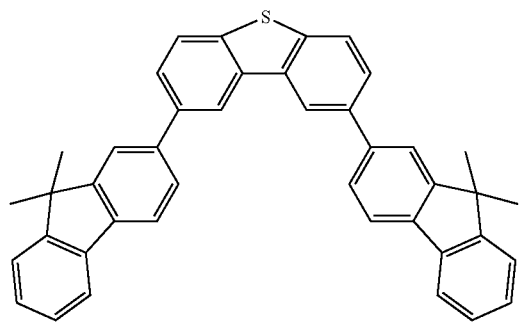

H-1

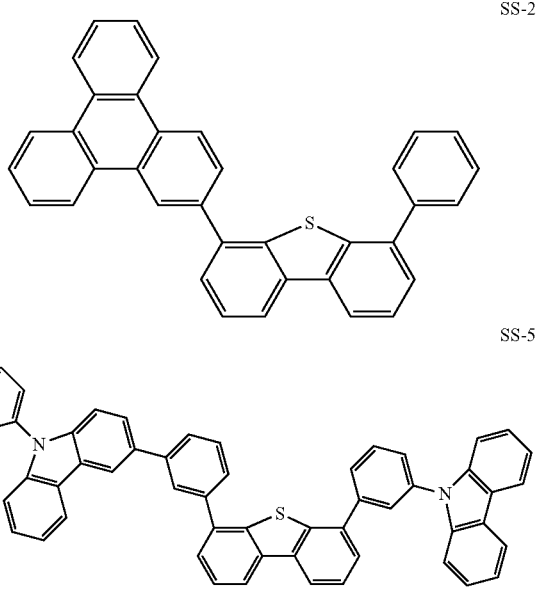

SS-2

SS-5

TABLE 4

| | Guest material | Host material | Luminance half-life (hr) |
|---|---|---|---|
| Example 16 | Ir-8 | B-4 | 220 |
| Comparative Example 1 | Ir-8 | H-1 | 55 |
| Example 17 | Ir-8 | A-5 | 210 |
| Comparative Example 2 | Ir-8 | SS-2 | 150 |
| Comparative Example 3 | Ir-8 | SS-5 | 10 |

As indicated by these results, the dibenzothiophene compound according to aspects of the present invention provides organic phosphorescence-emitting elements with a prolonged luminance half-life, compared with the compounds used in the comparative examples. In comparison between H-1 and its derivative having the same substituent introduced at the C4 and C5 positions of dibenzothiophene (B-4), the latter gave a longer luminance half-life. In comparison between SS-2 and its derivative having the same substituent introduced at the C4 and C5 positions (A-1), the latter gave a longer luminance half-life. In addition, the shortest luminance half-life was observed with SS-5, which had heteroaryl substituents.

These results emphasize that introducing the same kind of polycyclic aromatic hydrocarbon group into a dibenzothiophene compound at the C4 and C5 positions brings about the following advantages and prolongs the operation life of organic light-emitting elements thereby.

Advantage 1

Polycyclic aromatic hydrocarbon groups have a large excluded volume. When introduced at the C4 and C5 positions, therefore, they can protect the bonds between the sulfur atom (S) and the carbon atoms on the benzene rings from reacting with external agents.

Advantage 2

Having the same kind of polycyclic aromatic hydrocarbon group introduced at its C4 and C5 positions, the molecule is highly symmetric and thus highly stable in the form of an electron carrier and in its excited state.

Advantage 3

Containing no heteroatoms in the substituents at its C4 and C5 positions, the molecule has a high chemical stability.

Example 18, and Comparative Examples 4 and 5

Elements were prepared in the same way as in Example 1 except that the host material and the guest material were changed and that a hole-and-exciton-blocking layer was formed. The completed elements were tested for current efficiency at a luminance of 3000 cd/m². Results are summarized in Table 5. The structures of the compounds used in the comparative examples were as follows.

Chemical Formula 32

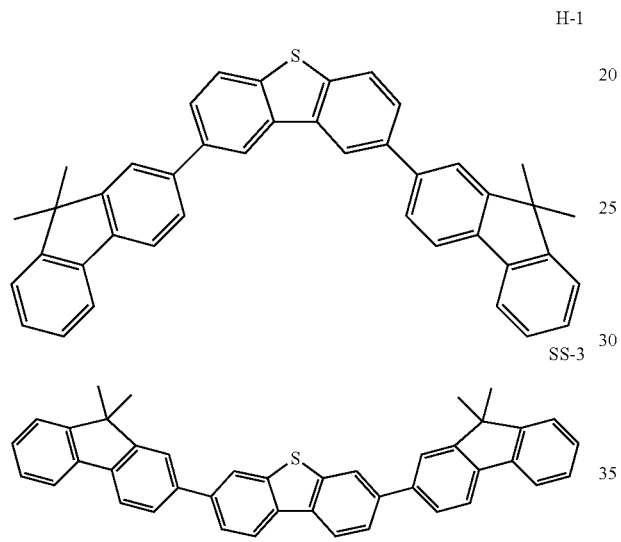

TABLE 5

| | Host material | Guest material | Current efficiency (cd/A) |
|---|---|---|---|
| Example 18 | Ir-8 | B-4 | 45 |
| Comparative Example 4 | Ir-8 | H-1 | 30 |
| Comparative Example 5 | Ir-8 | SS-3 | 3 |

As indicated by these results, the dibenzothiophene compound according to aspects of the present invention offers a higher light-emission efficiency in an organic phosphorescence-emitting element than those having the same substituent at different substitution positions. This is because the T1 of a dibenzothiophene compound reaches the highest level when a single kind of substituent is introduced at the substitution positions specified in the embodiment described above. As a result, organic light-emitting elements can generate light at a high efficiency.

In summary, the dibenzothiophene compound according to aspects of the present invention, which has the same kind of polycyclic aromatic hydrocarbon group introduced at the C4 and C5 positions on its dibenzothiophene skeleton, has a high level of T1 energy and is chemically stable. Using the dibenzothiophene compound according to aspects of the present invention in an organic light-emitting element will provide the element with a high light-emitting efficiency, resistance to degradation, and a high stability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-219481 filed Sep. 29, 2010, which is hereby incorporated by reference herein in its entirety.

What is claimed is:

1. A dibenzothiophene compound represented by General Formula 1 below:

Chemical Formula 1

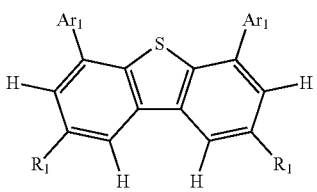

[1]

where:
$R_1$ is either a hydrogen atom or an unsubstituted phenyl group; and
$Ar_1$ is any of a phenanthrenyl group, a fluorenyl group, a triphenylenyl group, a naphthyl group, a chrysenyl group, and a pyrenyl group,
the phenanthrenyl group, the fluorenyl group, the triphenylenyl group, the naphthyl group, the chrysenyl group, and the pyrenyl group optionally may have a substituent selected from the group consisting of an alkyl group having one to four carbon atoms and an aryl group.

2. The dibenzothiophene compound according to claim 1, wherein:
the $Ar_1$ is any of a phenanthrenyl group, a fluorenyl group, and a triphenylenyl group.

3. The dibenzothiophene compound according to claim 1, wherein:
the $R_1$ is a hydrogen atom.

4. An organic light-emitting element comprising:
a pair of electrodes and
an organic compound layer,
the organic compound layer located between the pair of electrodes and containing the dibenzothiophene compound according to claim 1.

5. The organic light-emitting element according to claim 4, wherein:
the organic compound layer is used as at least one of a hole-and-exciton-blocking layer and a light-emitting layer.

6. The organic light-emitting element according to claim 4, wherein:
the organic compound layer is a light-emitting layer, the light-emitting layer contains a host material and a guest material, the host material comprises a plurality of constituents, and the constituents include the dibenzothiophene compound.

7. The organic light-emitting element according to claim 6, wherein:
the guest material is a phosphorescence-emitting material.

8. The organic light-emitting element according to claim 7, wherein:

the phosphorescence-emitting material is an iridium complex.

9. A display apparatus comprising:
a plurality of pixels,
each of the pixels having the organic light-emitting element according to claim 4 and a switching element connected to the organic light-emitting element.

10. An illumination apparatus comprising:
the organic light-emitting element according to claim 4 and
a switching element connected to the organic light-emitting element.

11. An image input apparatus comprising:
a display unit arranged to display an image, and
an input unit arranged to receive an image signal,
the display unit having a plurality of pixels, and each of the pixels having the organic light-emitting element according to claim 4 and a switching element connected to the organic light-emitting element.

12. A light source for electrophotographic image-forming apparatus comprising the organic light-emitting device according to claim 4.

* * * * *